(12) United States Patent
Geertsen

(10) Patent No.: US 10,842,417 B2
(45) Date of Patent: Nov. 24, 2020

(54) AUDIOLOGIC TEST PROBE WITH LOCKING MECHANISM, AND A COMPONENT FOR THE TEST PROBE

(71) Applicant: Natus Medical Incorporated, San Carlos, CA (US)

(72) Inventor: Thomas Geertsen, Slagelse (DK)

(73) Assignee: Natus Medical Incorporated, Pleasanton, CA (US)

( * ) Notice: Subject to any disclaimer, the term of this patent is extended or adjusted under 35 U.S.C. 154(b) by 0 days.

(21) Appl. No.: 14/589,909

(22) Filed: Jan. 5, 2015

(65) Prior Publication Data

US 2016/0183850 A1   Jun. 30, 2016

(30) Foreign Application Priority Data

Dec. 30, 2014  (DK) .................................. 2014 70839
Dec. 30, 2014  (EP) ..................................... 14200647

(51) Int. Cl.
*A61B 5/12* (2006.01)
*A61B 5/00* (2006.01)

(52) U.S. Cl.
CPC ............ *A61B 5/121* (2013.01); *A61B 5/6817* (2013.01)

(58) Field of Classification Search
CPC ............ A61B 5/12–128; A61B 5/6815; A61B 5/6817; A61F 11/08; A61F 2011/085; H04R 1/10; H04R 1/1016; H04R 1/1066; G01J 5/021
USPC .......... 600/559; 215/200–364; 220/212, 796; 74/570.3
See application file for complete search history.

(56) References Cited

U.S. PATENT DOCUMENTS

| | | | |
|---|---|---|---|
| 1,162,512 A * | 11/1915 | Prinz ..................... | F04B 47/026 74/570.3 |
| 6,299,584 B1 | 10/2001 | Iseberg | |
| 7,354,194 B2 * | 4/2008 | Walker ................... | G01J 5/021 374/158 |
| 8,308,353 B2 * | 11/2012 | Yamaguchi ............. | G01J 5/04 600/549 |
| 8,526,652 B2 * | 9/2013 | Ambrose ............. | H04R 1/1016 381/322 |

(Continued)

FOREIGN PATENT DOCUMENTS

| | | |
|---|---|---|
| CN | 203576509 U | 5/2014 |
| WO | WO 94/22372 A1 | 10/1994 |

(Continued)

OTHER PUBLICATIONS

Second Technical Examination—Intention to Grant dated Aug. 24, 2015 for corresponding Danish Patent Application No. PA 2014 70839, 3 pages.

(Continued)

*Primary Examiner* — David J. McCrosky
(74) *Attorney, Agent, or Firm* — Daniel C. Pierron; Widerman Malek, PL

(57) ABSTRACT

An audiologic test probe with locking mechanism, and a component for the test probe is disclosed. The probe for conducting an audiologic test comprises the locking mechanism, the probe comprising a probe body with a first probe opening to a first probe channel in the probe body, the probe comprising the locking mechanism for connecting a component with a first component opening to a first component channel.

10 Claims, 9 Drawing Sheets

(56) References Cited

U.S. PATENT DOCUMENTS

| | | | |
|---|---|---|---|
| 2005/0015018 A1 | 1/2005 | Dolphin et al. | |
| 2007/0112279 A1* | 5/2007 | Iseberg | A61B 5/03 600/559 |
| 2012/0191004 A1* | 7/2012 | Iseberg | A61B 5/6817 600/559 |

FOREIGN PATENT DOCUMENTS

| | | |
|---|---|---|
| WO | WO 2010/132359 A2 | 11/2010 |
| WO | WO 2010/132359 A3 | 11/2010 |
| WO | WO 2010/132359 A8 | 11/2010 |

OTHER PUBLICATIONS

Extended European Search Report dated Jun. 10, 2015 for corresponding EP Patent Application No. 14200647.7, 5 pages.
First Technical Examination dated Jul. 9, 2015 for corresponding Danish Patent Application No. PA 2014 70839, 4 pages.

* cited by examiner

AUDIOLOGIC TEST PROBE WITH LOCKING MECHANISM, AND A COMPONENT FOR THE TEST PROBE

RELATED APPLICATION DATA

This application claims priority to and the benefit of Danish Patent Application No. PA 2014 70839 filed on Dec. 30, 2014, pending, and European Patent Application No. 14200647.7 filed on Dec. 30, 2014, pending. The entire disclosures of both of the above applications are expressly incorporated by reference herein.

FIELD

The present disclosure relates to a locking mechanism for a hearing/audiologic test probe, such as a hearing test probe comprising a filter device, such as a filter device, wherein the filter device prevents cerumen, commonly known as earwax, from entering into a cavity comprising delicate equipment, such as a microphone and/or a speaker. The locking mechanism may be used in a locked position to retain the filter device and/or a probe tip and/or a probe tip comprising a filter device in its installed position, and in an unlocked position allow exchange of the filter device and/or a probe tip and/or a probe tip comprising a filter device. The hearing test probe may be a hearing test probe suitable to be used in performing audiologic tests, such as tympanometric and/or otoacoustic emission tests.

BACKGROUND

In order to perform an audiologic test a probe needs to be inserted into the ear canal of a person to be tested. The probe holds audible devices, such as a microphone and/or one or more speakers. These components may be damaged or altered by cerumen from the person's ear. Therefore a filter device is applied to the probe between the components of the probe and a distal end of the probe to be inserted into the ear canal.

Cerumen is trapped by the filter device. Therefore the filter device needs to be replaceable. For example, cerumen trapped in the filter device may alter acoustic properties of the filter device, thereby prompting the filter device to be replaced and/or cleaned. Furthermore, the filter device needs to be securely retained in its installed position when the probe is in use, and the filter device needs to be retained in the installed position in a manner which limits alteration to acoustic properties of the filter.

SUMMARY

Despite the known solutions there is still a need for a locking mechanism for a filter device, which is convenient and easy to use, and additionally provides a reliable, accurate and careful securing of the filter device, such as securing of the filter device in a hearing test probe.

Accordingly, a locking mechanism, and a probe for conducting an audiologic test comprising the locking mechanism are disclosed. The probe comprises a probe body with a first probe opening to a first probe channel in the probe body, the probe comprising the locking mechanism for connecting a component with a first component opening to a first component channel.

The locking mechanism comprises a probe wall extending along a main axis and having an inner surface and an outer surface. The probe wall forms a seat for receiving the component, and the probe wall surrounds the first probe opening.

The locking mechanism further comprises a coupling member with a center axis. The coupling member has a first position and a second position in relation to or relative to the probe body. The locking mechanism may be configured to lock the component to the probe body depending on the position of the coupling member, e.g. one of the positions may be a locked position and the other position may be an unlocked position.

The locking mechanism further comprises one or more engagement elements including a first engagement element, e.g. for engagement with a coupling element of the component. The first engagement element may be movable along a first engagement axis perpendicular or substantially perpendicular (e.g. ±5°) to the main axis when the coupling member is in the first position and/or in the second position.

Also disclosed is a component for an audiologic test probe, such as the disclosed test probe. The component comprises a coupling part for engagement with a locking mechanism of the audiologic test probe. The coupling part extends along a center axis with one or more coupling elements including a first coupling element for engagement with an engagement element of the locking mechanism.

The component may be a probe tip and/or a filter device, such as a cerumen filter, and/or a probe tip comprising a filter device, such as a cerumen filter. Further disclosed is a test probe system comprising a hearing test probe and one or more components, such as at least two components, as disclosed herein.

It is an advantage that the disclosed locking mechanism is convenient and easy to use, and additionally provides a reliable, accurate and careful securing of the component, such as securing a filter device or a probe tip in a hearing test probe.

A probe for conducting an audiologic test, the probe comprising a probe body with a first probe opening associated with a first probe channel in the probe body, the probe comprising a locking mechanism for connecting a component having a first component opening associated with a first component channel, the locking mechanism includes: a probe wall extending along a main axis and having an inner surface and an outer surface, the probe wall forming a seat for receiving the component, the probe wall surrounding the first probe opening; a coupling member with a center axis, the coupling member being moveable to a first position and to a second position in relation to the probe body, wherein the locking mechanism is configured to lock the component to the probe body depending on a position of the coupling member; and one or more engagement elements including a first engagement element for engagement with a coupling element of the component, wherein the first engagement element is movable along a first engagement axis perpendicular to the main axis when the coupling member is in the first position.

Optionally, when the coupling member is in the second position, the first engagement element is prevented from moving to a release position along the first engagement axis such that the component is locked to the probe.

Optionally, the locking mechanism is configured to lock the component to the probe body when the coupling member is in the second position.

Optionally, the coupling member is configured to move from the first position to the second position by rotation of the coupling member in relation to the probe body about the center axis.

Optionally, the coupling member is rotatable from the first position to the second position with an angular displacement that is anywhere from 10° to 360°.

Optionally, the coupling member is configured to move from the first position to the second position by movement of the coupling member along the main axis in relation to the probe body.

Optionally, the first engagement element comprises a first ball.

Optionally, the probe wall comprises a first cavity at least partly accommodating the first engagement element, the first cavity forming a first engagement stop for the first engagement element.

Optionally, the one or more engagement elements comprise a second engagement element for engagement with an additional coupling element of the component, wherein the second engagement element is movable along a second engagement axis perpendicular to the main axis when the coupling member is in the first position; wherein when the coupling member is in the second position, the second engagement element is prevented from moving to a release position along the second engagement axis; and wherein the probe wall comprises a first cavity at least partly accommodating the first engagement element, and a second cavity at least partly accommodating the second engagement element, the second cavity forming an engagement stop for the second engagement element.

Optionally, the coupling member comprises a first lock stop for the first engagement element when the coupling member is in the second position.

Optionally, the coupling member comprises a first release stop for the first engagement element when the coupling member is in the first position, wherein the first release stop is at a first release distance from the center axis, and the first lock stop is at a first lock distance from the center axis, wherein the first release distance is larger than the first lock distance.

Optionally, the probe wall has a non-circular cross section.

Optionally, the one or more engagement elements comprise a second engagement element, a third engagement element, and a fourth engagement element.

Optionally, the probe body has a second probe opening associated with a second probe channel in the probe body, and wherein the probe wall surrounds the second probe opening.

A component for an audiologic test probe, the component includes a coupling part for engagement with a locking mechanism of the audiologic test probe, the coupling part extending along a center axis and having one or more coupling elements including a first coupling element for engagement with an engagement element of the locking mechanism.

Other features, embodiments, and advantageous will be described below in the detailed description.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
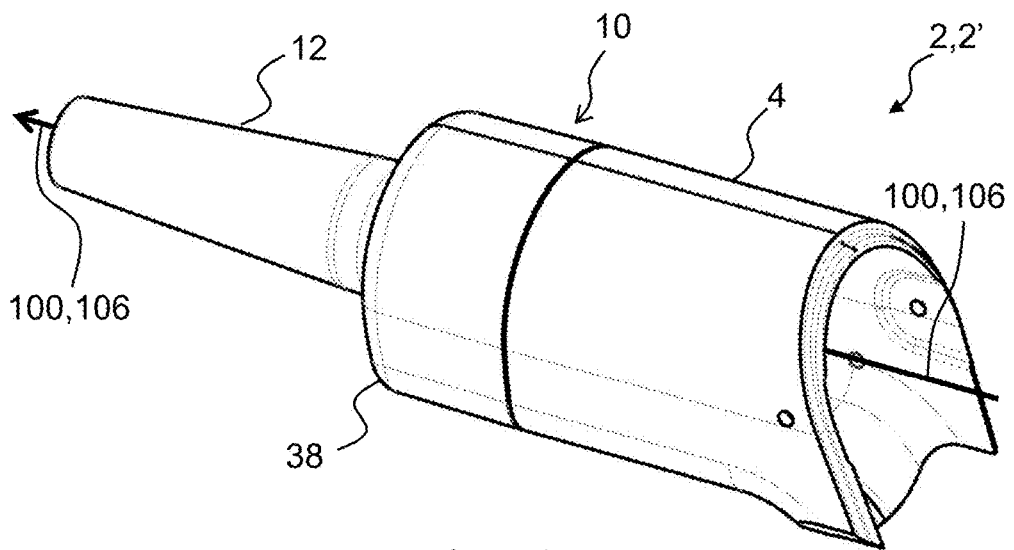
FIG. 1 illustrates an exemplary probe with a connected component.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The probe comprises the probe body. The probe body comprises the first probe opening to the first probe channel in the probe body. Alternatively or additionally, the probe body may have a plurality of probe openings to a plurality of probe channels in the probe body. For example, the probe body may have a second probe opening to a second probe channel in the probe body, and/or the probe may have a third probe opening to a third probe channel in the probe body, and/or the probe body may have a fourth probe opening to a fourth probe channel in the probe body. A plurality of probe channels and respective probe openings may provide openings and channels for different purposes. For example, the first probe opening to the first probe channel may be intended for providing sound, e.g. the first probe channel may be connected to a speaker, the second probe opening to the second probe channel may be intended for recording sound, e.g. the second probe channel may be connected to a microphone, and the third probe opening to the third probe channel may be intended for pressurizing, e.g. the third probe channel may be connected to a pump. A plurality of probe channels and respective probe openings may have similar purposes, e.g. a plurality of probe channels and respective probe openings may be intended for providing sound and/or recording sound and/or pressurizing.

The component has a first component opening to a first component channel. Alternatively or additionally, the component may have a plurality of component openings to a plurality of component channels. For example, the component may have a second component opening to a second component channel, and/or the component may have a third component opening to a third component channel, and/or the component may have a fourth component opening to a fourth component channel. A plurality of component channels and respective component openings may provide openings and channels for different purposes. For example, the first component opening to the first component channel may be intended for providing sound, e.g. the first component channel may be configured to be connected to a speaker, the second component opening to the second component channel may be intended for recording sound, e.g. the second component channel may be configured to be connected to a microphone, and the third component opening to the third component channel may be intended for pressurizing, e.g. the third component channel may be configured to be connected to a pump. A plurality of component channels and respective component openings may have similar purposes, e.g. a plurality of component channels and respective component openings may be intended for providing sound and/or recording sound and/or pressurizing.

The component channels may be configured to be connected to respective probe channels, e.g. the component openings may be configured to be connected to respective probe openings. For example, the first component opening may be configured to be connected to the first probe opening, and/or the second component opening may be configured to be connected to the second probe opening, and/or the third component opening may be configured to be connected to the third probe opening, and/or the fourth component opening may be configured to be connected to the fourth probe opening.

Connecting the component may comprise connecting the first component opening to the first probe opening and/or connecting the second component opening to the second probe opening and/or connecting the third component opening to the third probe opening and/or connecting the fourth component opening to the fourth probe opening and/or connecting the plurality of component openings to the plurality of probe openings.

An engagement element facilitates locking of the component to a test probe. A recess or a bore, such as a through-going bore, in the probe wall may form at least a part of an engagement element. A ball or an elongated member may constitute or form a part of an engagement element. A ball may be preferred because of the symmetric geometry facilitating assembly of the test probe. A flexible arm, e.g. with a protrusion at a distal end, may constitute or form part of an engagement element.

The one or more engagement elements include the first engagement element. The one or more engagement elements may comprise a second engagement element, a third engagement element, and/or a fourth engagement element, e.g. for engagement with one or more or respective coupling element(s) of the component. The one or more engagement elements may include a plurality of engagement elements. A plurality of engagement elements may facilitate a more stable connection and/or distributed contact forces between the component and the test probe.

A coupling element of the component may be a recess, such as a recess configured for engagement with an engagement element. For example, a coupling element may be a recess, e.g. forming part of a sphere. A coupling element may be a protrusion, a flexible arm and/or a ball.

An engagement element, such as the first engagement element, the second engagement element, the third engagement element, and/or the fourth engagement element may be movable along a respective engagement axis perpendicular to the main axis. For example, the second engagement element may be movable along a second engagement axis perpendicular or substantially perpendicular (e.g. ±5°) to the main axis. The third engagement element may be movable along a third engagement axis perpendicular or substantially perpendicular (e.g. ±5°) to the main axis. The fourth engagement element may be movable along a fourth engagement axis perpendicular or substantially perpendicular (e.g. ±5°) to the main axis.

An engagement element, such as the first engagement element, the second engagement element, the third engagement element, and/or the fourth engagement element may be movable along a respective engagement axis when the coupling member is in the first position.

The locking mechanism comprises a coupling member having a first position and a second position. The locking mechanism may be configured to lock the component to the probe body when the coupling member is in the second position. The first position may be an unlocked position. The component may be dislocated from the probe body when the coupling member is in the first position. The second position may be a locked position. The component may be locked in attachment with the probe body when the coupling member is in the second position.

The coupling member in the second position may prevent engagement elements, such as the first engagement element, the second engagement element, the third engagement element, and/or the fourth engagement element from moving to a release position along an engagement axis, such as the first engagement axis, the second engagement axis, the third engagement axis, and/or the fourth engagement axis.

The coupling member, e.g. in the second position, may prevent one or more engagement elements from moving to a release position along an engagement axis such that the component is locked to the probe.

The coupling member in the first position may be configured to allow one or more engagement elements, such as the first engagement element, the second engagement element, the third engagement element, and/or the fourth engagement element, to move to a release position, such as to move to a release position along one or more engagement axes. For example, the coupling member in the first position may allow the first engagement element to move to a release position along the first engagement axis, and/or the coupling member in the first position may allow the second engagement element to move to a release position along the second engagement axis.

The coupling member may be configured to move from the first position to the second position and/or from the second position to the first position by rotation of the coupling member in relation to the probe body about the center axis. The coupling member may be rotated from the first position to the second position with an angular displacement in the range from 10° to 360°, such as in the range from 10° to 40°, such as in the range from 20° to 30°, such as 25°.

The coupling member may be configured to move from the first position to the second position and/or from the second position to the first position by movement of the coupling member along the main axis in relation to the probe body.

Movement of the coupling member along the main axis may be caused by simultaneous rotation of the coupling member in relation to the probe body about the center axis, e.g. the coupling member may be threaded. Alternatively, movement of the coupling member along the main axis may be independent of rotation of the coupling member.

The coupling member and the probe body may be biased, e.g. by a spring. For example, the coupling member may be biased to be in a locked position, such as the second position.

The coupling member may comprise one or more lock stops for the one or more engagement elements in a first release direction along the first engagement axis when the coupling member is in the second position. For example, the coupling member may comprise a first lock stop for the first engagement element in a first release direction along the first engagement axis when the coupling member is in the second position. Additionally or alternatively, the coupling member may comprise a second lock stop for the second engagement element in a second release direction along the second engagement axis when the coupling member is in the second position. A release direction, such as the first release direction and/or the second release direction may be a direction radially extending from the center axis.

The coupling member may comprise one or more release stops for the one or more engagement elements in their respective release directions when the coupling member is in the first position. For example, the coupling member may comprise a first release stop for the first engagement element in the first release direction when the coupling member is in the first position. Additionally or alternatively, the coupling member may comprise a second release stop for the second engagement element in the second release direction when the coupling member is in the first position.

The one or more release stops may have respective release distances to the center axis. The one or more lock stops may have respective lock distances to the center axis. The release distances may be larger than the respective lock distances. For example, the first release stop may have a first release distance to the center axis and the first lock stop may have a first lock distance to the center axis, wherein the first release distance is larger than the first lock distance. Additionally or alternatively, the second release stop may have a second release distance to the center axis and the second lock stop may have a second lock distance to the center axis, wherein the second release distance is larger than the second lock distance.

One or more engagement elements, such as the first engagement element, the second engagement element, the third engagement element, and/or the fourth engagement element, may be a flexible arm comprising a protrusion. For example, the first engagement element may be a first flexible arm comprising a protrusion, and/or the second engagement element may be a second flexible arm comprising a protrusion, and/or the third engagement element may be a third flexible arm comprising a protrusion, and/or the fourth engagement element may be a fourth flexible arm comprising a protrusion.

One or more engagement elements, such as the first engagement element the second engagement element, the third engagement element, and/or the fourth engagement element, may be a ball. A ball may be a sphere. For example, the first engagement element may be a first ball, and/or the second engagement element may be a second ball, and/or the third engagement element may be a third ball, and/or the fourth engagement element may be a fourth ball. The ball(s) may be made of magnetic material, such as a magnetic metal or alloy. The ball(s) may be made of metal or a metal alloy. The different balls may have the same or different size. Different sized balls may facilitate optimum locking in a limited sized test probe.

The probe wall comprises an outer surface and an inner surface. The inner surface of the probe wall may have a non-circular cross section, such as an oval cross section, a rectangular cross section, a polygon cross section, and/or a cross section comprising a radial projection. A non-circular cross section may provide increased certainty that the component is positioned correctly in the seat formed by the wall. Furthermore, a non-circular cross section may prevent adverse rotation of the component relative to the probe when the component is positioned in the seat.

The probe wall surrounds the first probe opening. Additionally or alternatively, the probe wall may surround one or more of the plurality of probe openings. For example, the probe wall may surround the second probe opening, and/or the probe wall may surround the third probe opening, and/or the probe wall may surround the fourth probe opening.

The probe wall may comprise one or more cavities at least partly accommodating the one or more engagement elements. The one or more cavities may form first engagement stops for the one or more engagement elements. For example, the probe wall may comprise a cavity at least partly accommodating an engagement element, such as the first engagement element, the second engagement element, the third engagement element, or the fourth engagement element. The cavity may form a first engagement stop for an engagement element in an engagement direction. For example, the probe wall may comprise a first cavity at least partly accommodating the first engagement element. The first cavity may form a first engagement stop for the first engagement element, such as a first engagement stop for the first engagement element in a first engagement direction along the first engagement axis. Alternatively or additionally, the probe wall may comprise a second cavity at least partly accommodating the second engagement element. The second cavity may form a first engagement stop for the second engagement element in a second engagement direction along the second engagement axis.

An engagement direction may be opposite to a respective release direction. For example, the first engagement direction may be opposite to the first release direction, and/or the second engagement direction may be opposite to the second release direction.

The one or more engagement elements, such as the first engagement element and/or the second engagement element and/or the third engagement element and/or the fourth engagement element, may be made of plastic. For example, the one or more engagement elements may be plastic flexible arms. For example the first engagement element and/or the second engagement element and/or the third engagement element and/or the fourth engagement element, may be a plastic flexible arms.

The one or more engagement elements, such as the first engagement element and/or the second engagement element and/or the third engagement element and/or the fourth engagement element, may be made of metal. For example, the one or more engagement elements may be metal balls. For example the first engagement element and/or the second engagement element and/or the third engagement element and/or the fourth engagement element, may be a metal ball.

Utilizing metal may provide for an easy assembly process. For example, the metal balls may be retained in the cavities while mounting the coupling member by positioning a magnet inside the probe. After mounting the coupling member, the magnet may be removed.

Throughout, the same reference numerals are used for identical or corresponding parts.

FIG. 1 illustrates an exemplary probe 2, 2' with a connected component 12. The component 12 is in this depicted example a probe tip configured to be inserted into the ear of a user for conducting an audiologic test. The probe comprises a probe body 4.

The probe 2, 2' furthermore comprises a locking mechanism 10, 10' for connecting the component 12 to the probe body 4. The locking mechanism 10, 10' comprises a coupling member 38 with a center axis 106. The coupling member 38 has a first position and a second position relative to the probe body 4. The coupling member 38 may be configured to move from the first position to the second position and/or from the second position to the first position by rotation of the coupling member 38 in relation to the probe body 4 about the center axis 106.

Figure 2:
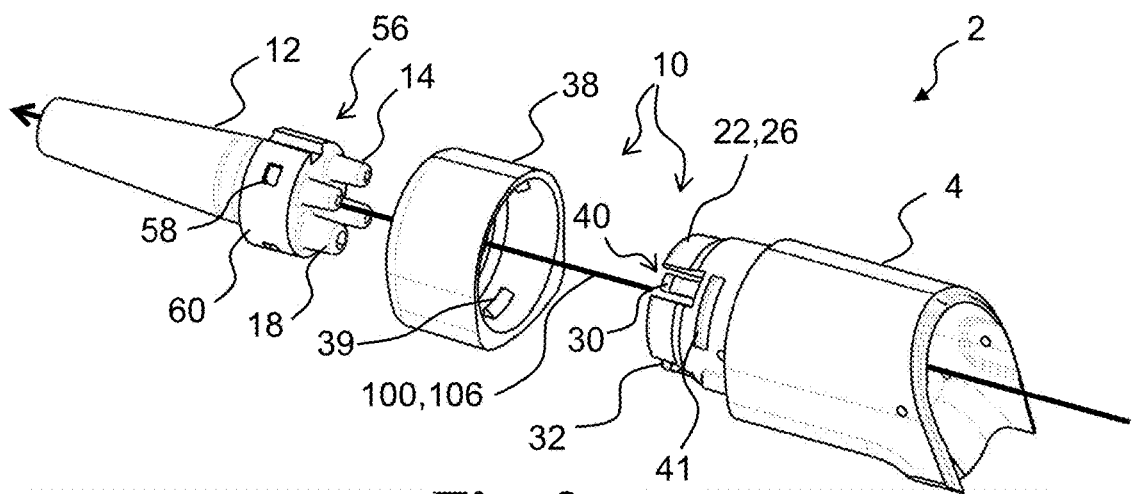
FIG. 2 is an exploded view of an exemplary probe with a component.

FIG. 2 is an exploded view of the exemplary probe 2 as shown in FIG. 1. FIG. 2 also shows the component 12 having a first component opening 14 to a first component channel. The component 12 shown in FIG. 2 has a plurality of component openings to a plurality of component channels including the first component opening 14 to the first component channel and a second component opening 18 to a second component channel.

The probe body 4 has a first probe opening to a first probe channel (not visible in FIG. 2). The probe body 4 may further have a plurality of openings to a plurality of probe channels including the first probe opening to the first probe channel and a second probe opening to a second probe channel. The probe body 4 may comprise a plurality of parts, e.g. including a primary part and/or a secondary part (not shown).

The locking mechanism 10 may be configured for connecting the first probe opening to the first component opening 14 and/or for connecting the second probe opening to the second component opening 18.

The locking mechanism 10 comprises a probe wall 22 extending along a main axis 100. The probe wall 22 has an inner surface and an outer surface 26. The probe wall 22 forms a seat for receiving the component 12. The probe wall 22 surrounds the first probe opening. The probe wall 22 may surround the plurality of probe openings.

The locking mechanism 10 further comprises one or more engagement elements 30, 32 including a first engagement element 30. In FIG. 2, the one or more engagement elements further includes a second engagement element 32. The one or more engagement elements, such as the first engagement element 30 and/or the second engagement element 32, are configured for engagement with a coupling element 58 of the component 12 when the component 12 is positioned in the seat formed by the probe wall 22. The one or more engagement elements 30, 32, such as the first engagement element 30 and/or the second engagement element 32 is movable perpendicular to the main axis 100, such as in a radial direction. The one or more engagement elements 30, 32, such as the first engagement element 30 and/or the second engagement element 32 may also be movable in a direction parallel to the main axis 100, such as in a longitudinal direction.

The coupling member 38 in one of the first position and the second position, such as the second position, is configured to prevent the first engagement element 30 and/or the second engagement element 32 from moving to a release position such that the component 12 is locked to the probe 2. The coupling member 38 in the other of the first position and the second position, such as the first position, is configured to allow the first engagement element 30 and/or the second engagement element 32 to move to a release position such that the component 12 is not locked to the probe.

The probe wall 22 comprises a first cavity 40, such as in the form of a slit, at least partly accommodating the first engagement element 30. The probe wall 22 may comprise one or more cavities including the first cavity 40. The one or more cavities may at least partly accommodate the one or more engagement elements 30, 32. The one or more cavities may comprise a second cavity at least partly accommodating the second engagement element 32.

The coupling member 38 and the probe body 4 may be configured to be attached to each other, such that the coupling member 38 is movable between positions, such as between the first position and the second position, but is retained attached to the probe body 4. For example, the coupling member 38 and/or the probe body 4 may comprise attachment members.

The coupling member 38 optionally comprises a primary attachment member 39, e.g. in the form of a protrusion as illustrated, and/or a plurality of attachment members including the primary attachment member 39. The probe body 4 optionally comprises a secondary attachment member 41, e.g. in the form of a recess as illustrated, and/or a plurality of secondary attachment members including the secondary attachment member. A primary attachment member, such as the primary attachment member 39, is configured to engage with a secondary attachment member, such as the secondary attachment member 41.

Provision of attachment members, such as primary attachment members and/or secondary attachment members, may provide that the coupling member may be click-locked to the probe body 4.

The component 12 comprises a coupling part 56 extending along the center axis 106. The coupling part has one or more coupling elements, such as a first coupling element 58 in an outer surface 60 for engagement with the one or more engagement elements 30, 32, such as the first engagement element 30 of the locking mechanism 10. The coupling part 56 may have a plurality of coupling elements 58 for engagement with a plurality of engagement elements 30, 32 of the locking mechanism 10.

In the depicted example, the one or more engagement elements 30, 32 are flexible arms, and the coupling elements 58 of the component are recesses adapted to receive at least a protruding part of the one or more engagement elements 30, 32.

The locking mechanism 10 further comprises the coupling member 38 with the center axis 106. The coupling member 38 has a first position and a second position. The coupling member 38 may be configured to move from the first position to the second position and/or from the second position to the first position by rotation of the coupling member 38 in relation to the probe body 4 about the center axis 106. For example, the coupling member may be rotated from the first position to the second position and/or from the second position to the first position with an angular displacement in the range of 5° to 360°, such as in the range of 10° to 90°, such as in the range of 20° to 60°, such as 25° or less.

Alternatively or additionally, the coupling member 38 may be configured to move from the first position to the second position and/or from the second position to the first position by movement of the coupling member along the main axis 100 in relation to the probe body 4. Movement of the coupling member 38 along the main axis 100 may be caused by simultaneous rotation of the coupling member 38 in relation to the probe body 4 about the center axis 106.

Alternatively, movement of the coupling member 38 along the main axis 100 may be independent of rotation of the coupling member 38.

Figure 3:
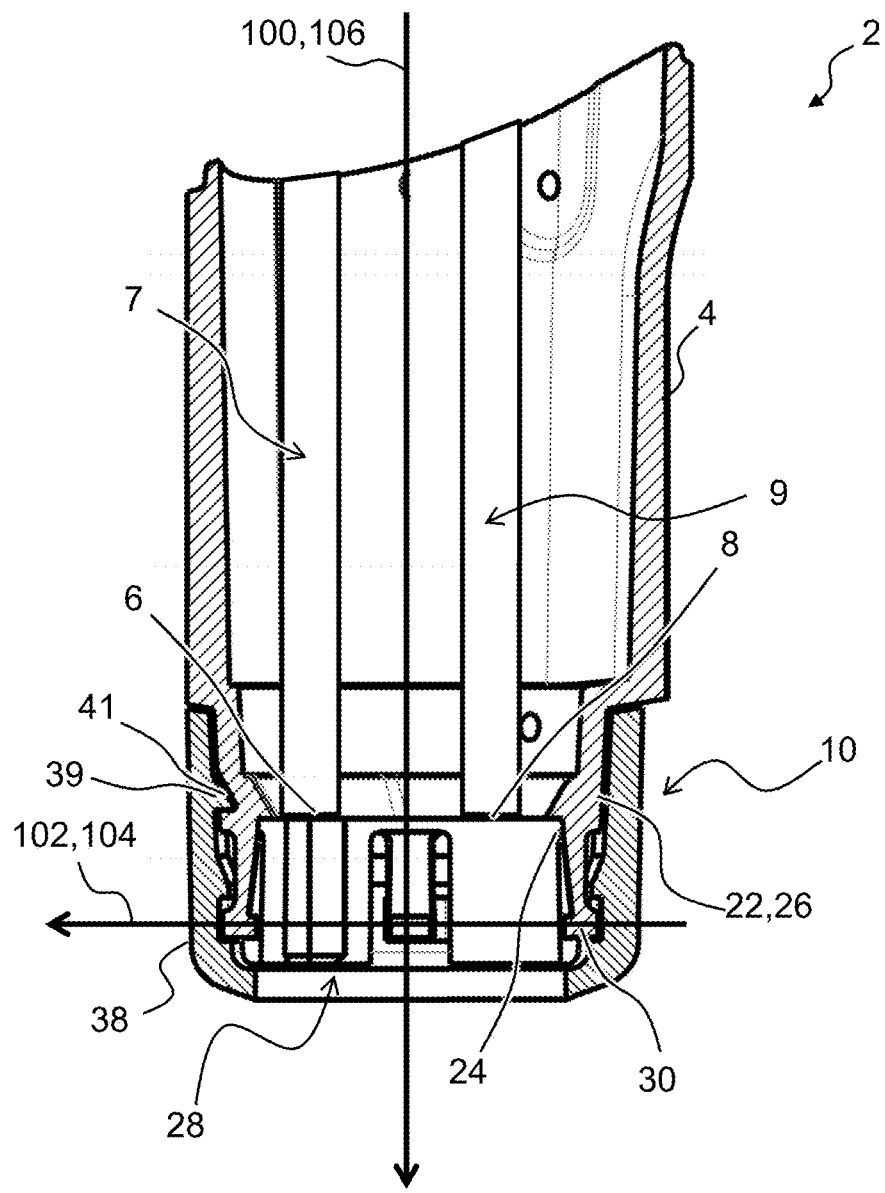
FIG. 3 is a longitudinal section of an exemplary probe.

FIG. 3 is a longitudinal section of an exemplary probe 2. The probe 2 comprises a probe body 4 with a first probe opening 6 to a first probe channel 7 in the probe body 4. In the depicted example, the probe 2 further comprises a second probe opening 8 to a second probe channel 9.

The probe 2 comprises a locking mechanism 10 for connecting a component (FIG. 2). The locking mechanism 10 comprises a probe wall 22 extending along a main axis 100 and having an inner surface 24 and an outer surface 26. The probe wall 22 forms a seat 28 for receiving the component. The probe wall 22 surrounds the first probe opening 6. The probe body 4 comprises a second probe opening 8 to a second probe channel 9. The probe wall 22 surrounds the second probe opening 8.

The locking mechanism 10 further comprises one or more engagement elements including a first engagement element 30 for engagement with a coupling element of the component. The first engagement element 30 is movable along a first engagement axis 102, e.g. in a first engagement direction 104. The first engagement axis 102 is perpendicular to the main axis 100. The first engagement axis 102 may alternatively be substantially perpendicular to the main axis, such as between 80° and 100°.

The locking mechanism 10 further comprises a coupling member 38 with a center axis 106. The locking mechanism 10 is configured to lock the component to the probe body 4 depending on the position of the coupling member 38, e.g. the locking mechanism 10 may be configured to lock the component to the probe body 4 when the coupling member 38 is in one position, and the locking mechanism 10 may be configured to not lock the component to the probe body 4 when the coupling member 38 is in another position.

The coupling member 38 has a first position and a second position. The coupling member 38 in the first position is configured to allow the first engagement element 30 to move to a release position. The coupling member 38 in the second position is configured to prevent the first engagement element 30 from moving to the release position.

The first engagement element 30 may be movable in a first release direction along the engagement axis 102. The first release direction may be opposite the first engagement direction 104.

Figures 4A, 4B:
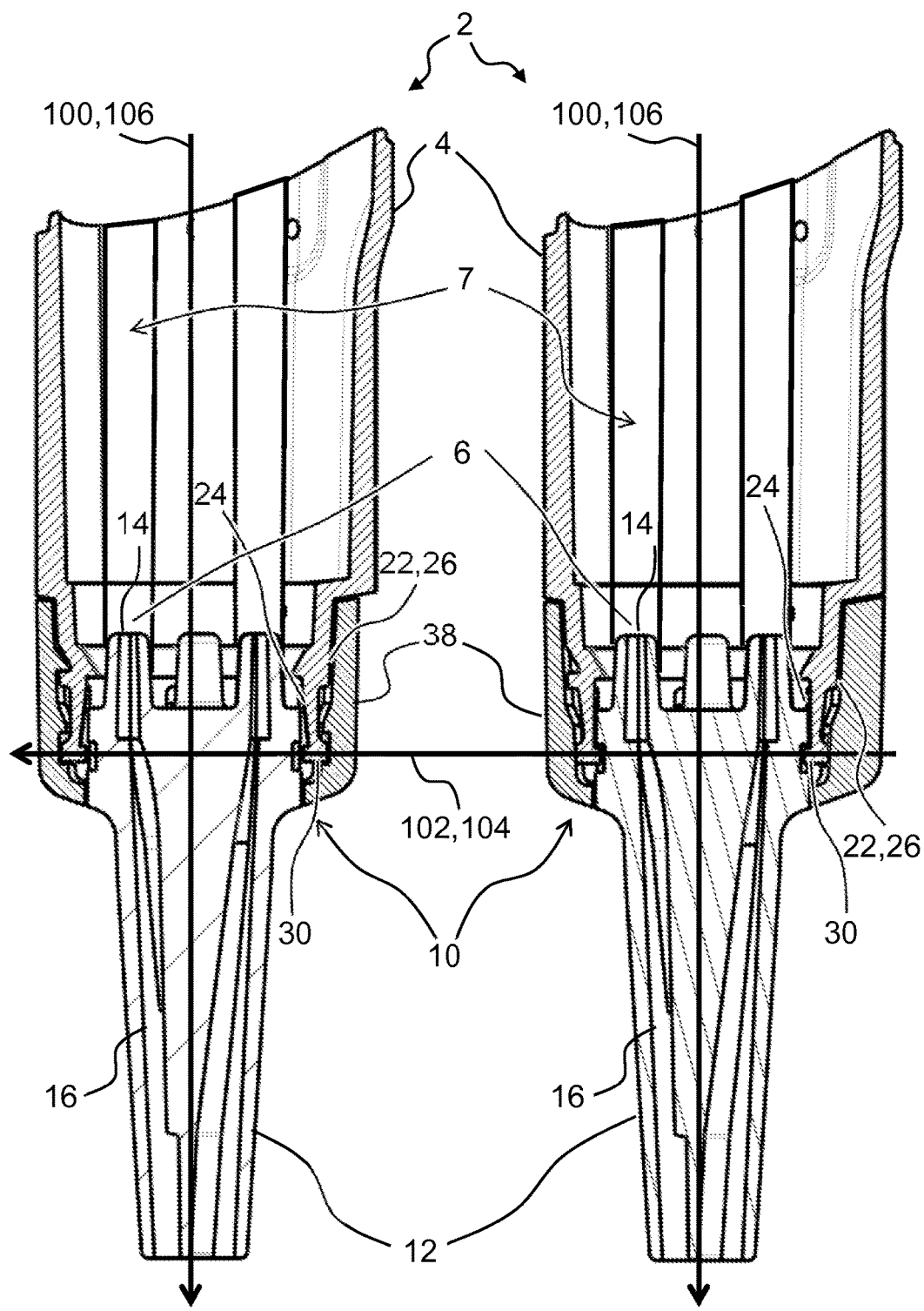
FIG. 4a-b is longitudinal sections of an exemplary probe with a component.

FIG. 4a and FIG. 4b are longitudinal sections of an exemplary probe 2 with an attached component 12.

In FIG. 4a, the first engagement element 30 is in a release position, wherein the component 12 is movable relative to the probe body 4 along the main axis 100. The component 12 may be detached from the probe body 4 when the first engagement element 30 is in the release position, as illustrated in FIG. 4a. In FIG. 4b, the first engagement element 30 is in an engagement position, wherein the component 12 is restricted from moving relative to the probe body 4 along the main axis 100. The component 12 is locked to the probe body 4 when the first engagement element 30 is in the engagement position, as illustrated in FIG. 4b.

In FIG. 4a, the coupling member 38 is in the first position, and in FIG. 4b the coupling member 38 is in the second position. The coupling member 38 in the first position (FIG. 4a) allows the first engagement element 30 to move along a first engagement axis 102, e.g. the coupling member 38 in the first position (FIG. 4a) allows the first engagement element 30 to move between the release position and the engagement position. The coupling member 38 in the second position (FIG. 4b) prevents the first engagement element 30 to move along the first engagement axis 102, e.g. the coupling member 38 in the second position (FIG. 4b) locks the first engagement element 30 in the engagement position.

The first engagement axis 102 is perpendicular to the main axis 100, and/or spanning an angle between 80° and 100°. The first engagement element 30 may move from the release position to the engagement position in a first engagement direction 104 along the first engagement axis 102. The first engagement element 30 may move from the engagement position to the release position in a first release direction, e.g. opposite the first engagement direction 104, along the first engagement axis 102.

The first engagement element 30 shown in the depicted example is biased towards the release position. Thus, when the coupling member 38 is in the first position (FIG. 4a) the first engagement element 30 is in the release position. The bias of the first engagement element is caused by the cast shape of the first engagement element 30 being a flexible arm.

In FIGS. 4a and 4b it is further illustrated that the component 12 comprises a first component opening 14 to a first component channel 16.

Figure 5:
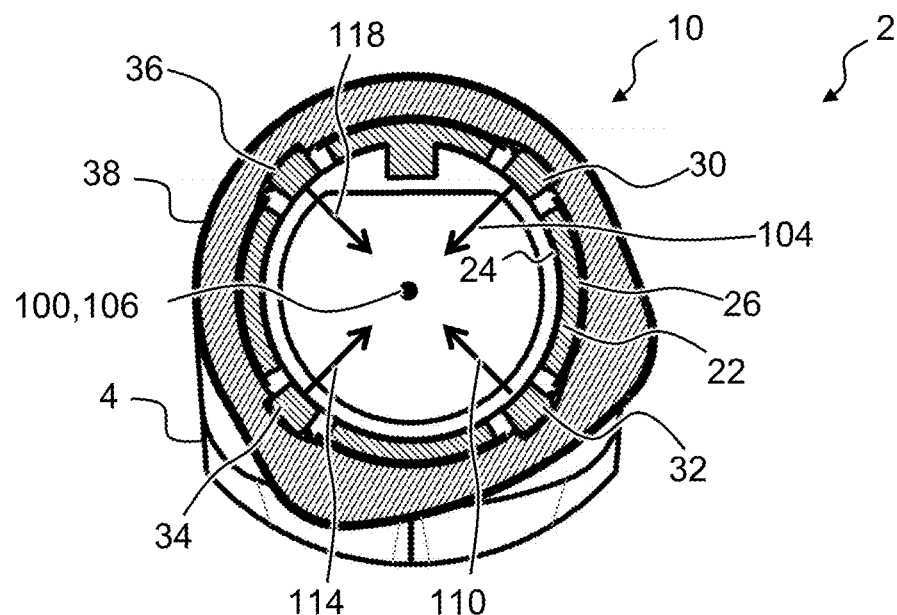
FIG. 5 is a cross section of an exemplary probe with a coupling member in a first position.

FIG. 5 is a cross section of an exemplary probe 2 with a coupling member 38 in a first position. The locking mechanism 10 of the exemplary probe 2 comprises one or more engagement elements 30, 32, 34, 36. In the depicted example, the locking mechanism 10 comprises a first engagement element 30, a second engagement element 32, a third engagement element 34, and a fourth engagement element 36.

The one or more engagement elements 30, 32, 34, 36 has an engagement position and a release position. In FIG. 5, the one or more engagement elements 30, 32, 34, 36 are in their release positions. In the depicted example, the one or more engagement elements 30, 32, 34, 36 are flush with the inner surface 24 of the probe wall 22 in their release positions.

The coupling member 38 in the first position, as shown in FIG. 5, allows the one or more engagement elements 30, 32, 34, 36 to move between their engagement positions and their release positions. In the depicted example, the one or more engagement elements 30, 32, 34, 36 are shown in their release position. The one or more engagement elements 30, 32, 34, 36 may move to the release position due to bias, e.g. the engagement elements 30, 32, 34, 36 are biased towards their release position, or the one or more engagement elements 30, 32, 34, 36 may be pushed to their release position by the component being removed from the probe body 4, e.g. by coupling elements of the component having a tapered surface.

The first engagement element 30 is movable in a first engagement direction 104 along a first engagement axis perpendicular to the main axis 100. The first engagement element 30 is movable in the first engagement direction 104 from the release position to the engagement position.

The second engagement element 32 is movable in a second engagement direction 110 along a second engagement axis perpendicular to the main axis 100. The second engagement element 32 is movable in the first engagement direction 110 from the release position to the engagement position.

The third engagement element 34 is movable in a third engagement direction 114 along a third engagement axis perpendicular to the main axis 100. The third engagement element 34 is movable in the third engagement direction 114 from the release position to the engagement position.

The fourth engagement element 36 is movable in a fourth engagement direction 118 along a fourth engagement axis perpendicular to the main axis 100. The fourth engagement element 36 is movable in the fourth engagement direction 118 from the release position to the engagement position.

One or more of the first, second, third, and/or fourth engagement elements 30,32,34,36 may also be movable in one or more directions not perpendicular to the main axis 100.

Furthermore, FIG. 5 shows that the inner surface 24 of the probe wall 22 has a non-circular cross section. Specifically in the depicted example, the probe wall 22 comprises a projection preventing rotation and misalignment of the component when the component is inserted in the seat formed by the probe wall.

Figure 6:
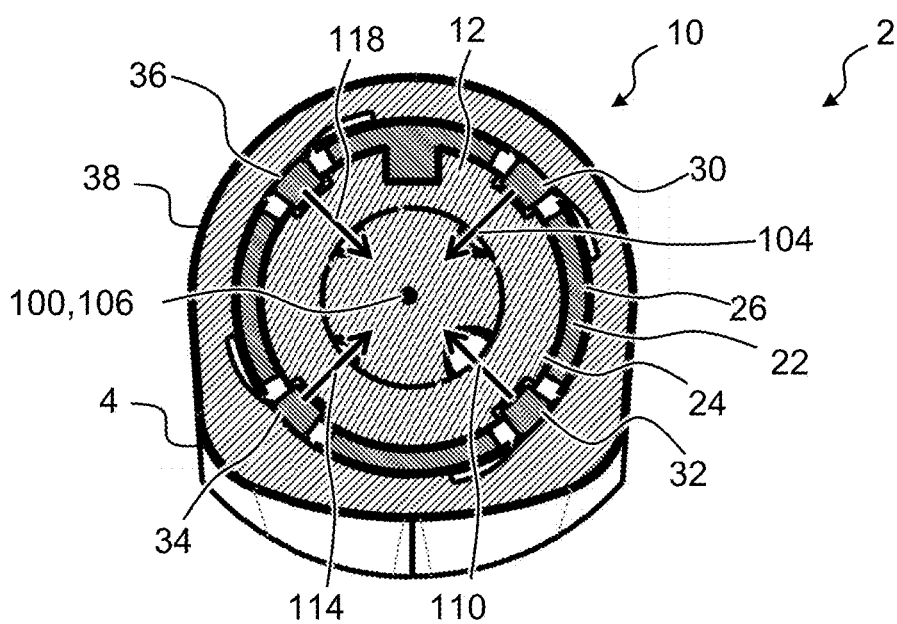
FIG. 6 is a cross section of an exemplary probe with a coupling member in a second position.

FIG. 6 is a cross section of the exemplary probe 2 of FIG. 5 with the coupling member 38 in a second position. In FIG. 6 a component 12 has been positioned in the seat formed by the probe wall 22.

The coupling member 38 has been moved from the first position, as illustrated in FIG. 5, to the second position, as illustrated in FIG. 6, by rotation of the coupling member 38 in relation to the probe body 4 about the center axis 106 of the coupling member 38. The coupling member 38 is rotated from the first position to the second position with an angular displacement of approximately 25°.

In FIG. 6, the one or more engagement elements 30, 32, 34, 36 are in their respective engagement positions. In their engagement positions, the one or more engagement elements 30, 32, 34, 36 may form a protrusion from the inner surface 24 of the probe wall 22 in their respective engagement directions 104, 110, 114, 118, e.g. perpendicular to the main axis 100. In their engagement positions, the one or more engagement elements 30, 32, 34, 36 may be flush with an outer surface 26 of the probe wall 22. In their engagement positions, the one or more engagement elements 30, 32, 34, 36 engage with coupling elements of the component 12.

In the depicted example, upon moving the coupling member 38 from the first position (FIG. 5) to the second position (FIG. 6), the coupling member 38 is configured to cause the one or more engagement elements 30, 32, 34, 36 to move to their engagement positions, e.g. in their respective engagement directions 104, 110, 114, 118.

Figure 7:
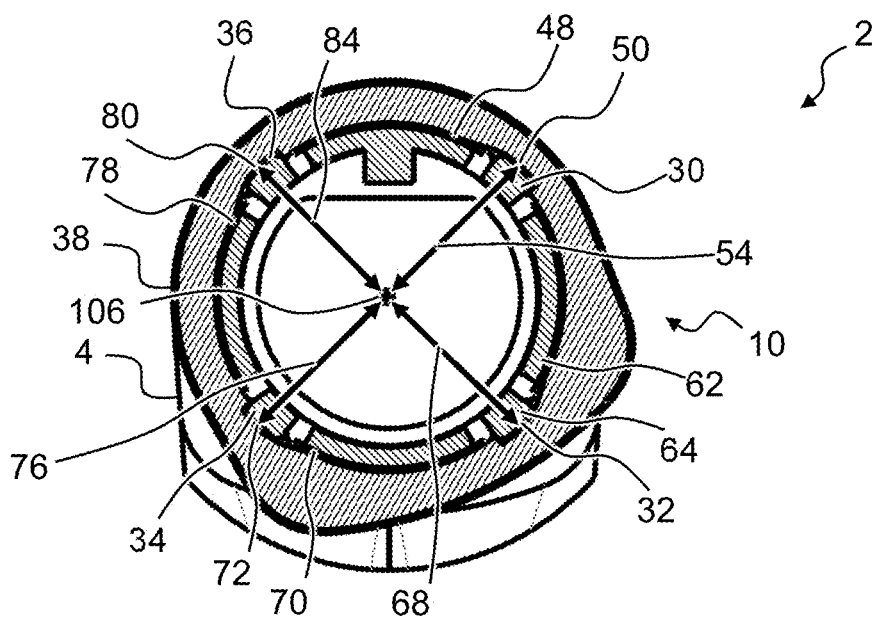
FIG. 7 is a cross section of an exemplary probe with a coupling member in a first position.
Figure 8:
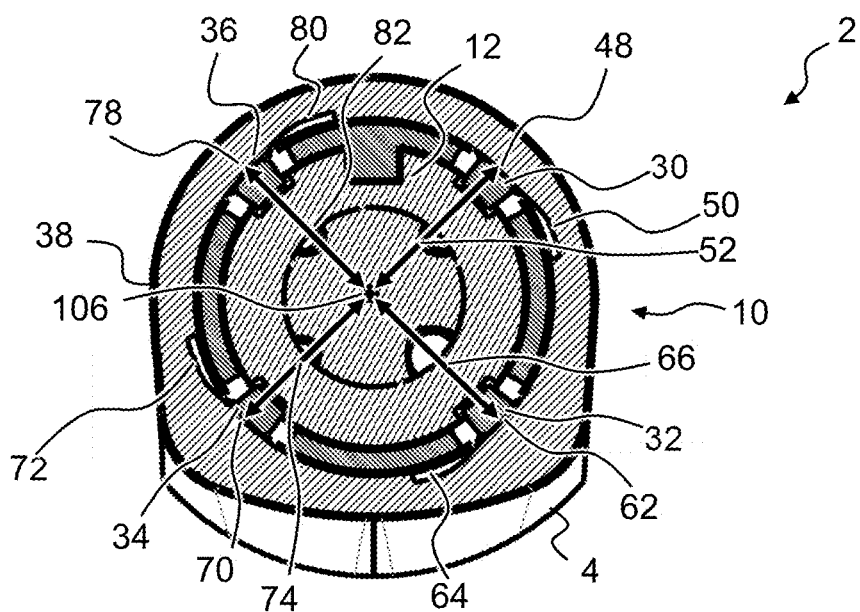
FIG. 8 is a cross section of an exemplary probe with a coupling member in a second position.

FIGS. 7 and 8 are cross sections of the exemplary probe 2 of FIGS. 5-6 with the coupling member 38 in the first position (FIG. 7) and second position (FIG. 8). In FIG. 8 a component 12 has been positioned in the seat formed by the probe wall 22.

The coupling member 38 comprises one or more lock stops 48, 62, 70, 78 for the one or more engagement elements 30, 32, 34, 36. The coupling member 38 comprises a first lock stop 48 for the first engagement element 30. The coupling member 38 comprises a second lock stop 62 for the second engagement element 32. The coupling member 38 comprises a third lock stop 70 for the third engagement element 34. The coupling member 38 comprises a fourth lock stop 78 for the fourth engagement element 36.

The coupling member 38 comprises one or more release stops 50, 64, 72, 80 for the one or more engagement elements 30, 32, 34, 36. The coupling member 38 comprises a first release stop 50 for the first engagement element 30. The coupling member 38 comprises a second release stop 64 for the second engagement element 32. The coupling member 38 comprises a third release stop 72 for the third engagement element 34. The coupling member 38 comprises a fourth release stop 80 for the fourth engagement element 36.

The one or more release stops 50, 64, 72, 80 are configured to form stops for the one or more engagement elements 30, 32, 34, 36 in release directions along their engagement axes, e.g. opposite their respective engagement directions, when the coupling member 38 is in the first position, as shown in FIG. 7.

The one or more lock stops 48, 62, 70, 78 are configured to form stops for the one or more engagement elements 30, 32, 34, 36 in release directions along their engagement axes, e.g. opposite their respective engagement directions, when the coupling member 38 is in the second position, as shown in FIG. 8.

The one or more lock stops 48, 62, 70, 78 have respective lock distances 52, 66, 74, 82 to the center axis. The one or more release stops 50, 64, 72, 80 have respective release distances 54, 68, 76, 84 to the center axis. A release distance 54, 68, 76, 84 is larger than its respective lock distance 52, 66, 74, 82.

The first lock stop 48 has a first lock distance 52 to the center axis 100. The first release stop 50 has a first release distance 54 to the center axis. The first release distance 54 is larger than the first lock distance 52.

The second lock stop 62 has a second lock distance 66 to the center axis 100. The second release stop 64 has a second release distance 68 to the center axis. The second release distance 68 is larger than the second lock distance 66.

The third lock stop 70 has a third lock distance 74 to the center axis 100. The third release stop 72 has a third release distance 76 to the center axis. The third release distance 76 is larger than the third lock distance 74.

The fourth lock stop 78 has a fourth lock distance 82 to the center axis 100. The fourth release stop 80 has a fourth release distance 84 to the center axis. The fourth release distance 84 is larger than the fourth lock distance 82.

The coupling member 38 may comprise a gradual transition, as shown in FIGS. 7 and 8, between a lock stop 48, 62, 70, 78 and its respective release stop 50, 64, 72, 80, such that upon moving the coupling member 38 from the first position to the second position, the coupling member 38 causes the one or more engagement elements, such as the first engagement element 30, the second engagement element 32, the third engagement element 34, and/or the fourth engagement element 36, to move from their release positions to their engagement positions, e.g. to move in their respective engagement directions.

FIGS. 9-15 illustrate an exemplary probe 2'.

Figure 9:
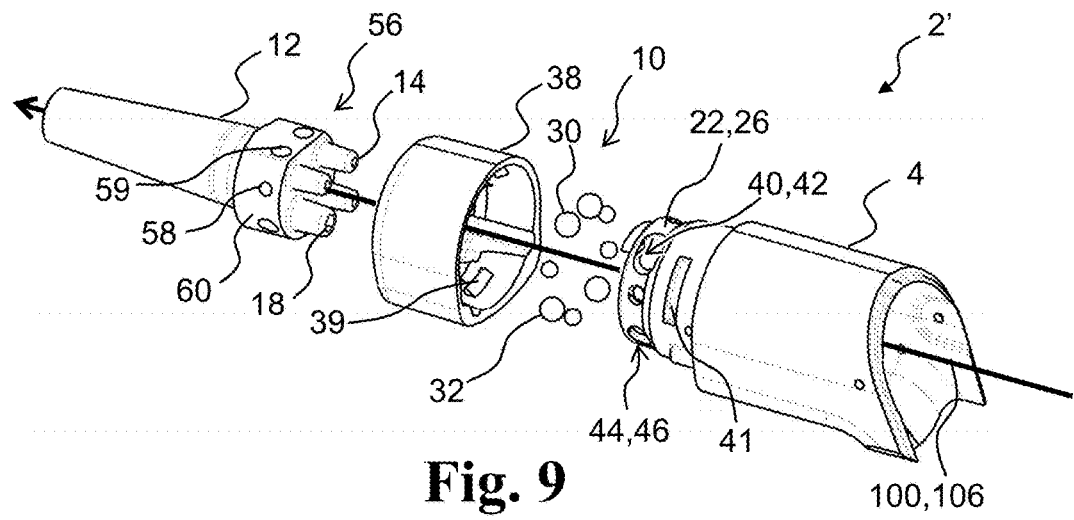
FIG. 9 is an exploded view of an exemplary probe with a component.

FIG. 9 is an exploded view of the exemplary probe 2' as shown in FIG. 1. FIG. 9 also shows the component 12 having a first component opening 14 to a first component channel. The component 12 shown in FIG. 9 has a plurality of component openings to a plurality of component channels including the first component opening 14 to the first component channel and a second component opening 18 to a second component channel.

The probe body 4 has a first probe opening to a first probe channel (not visible in FIG. 9). The probe body 4 may further have a plurality of openings to a plurality of probe channels including the first probe opening to the first probe channel and a second probe opening to a second probe channel.

The locking mechanism 10 may be configured for connecting the first probe opening to the first component opening 14 and/or for connecting the second probe opening to the second component opening 18.

The locking mechanism 10 comprises a probe wall 22 extending along a main axis 100. The probe wall 22 has an inner surface and an outer surface 26. The probe wall 22 forms a seat for receiving the component 12. The probe wall 22 surrounds the first probe opening. The probe wall 22 may surround the plurality of probe openings.

The locking mechanism 10 further comprises one or more engagement elements 30, 32 including a first engagement element 30. In FIG. 9, the one or more engagement elements further includes a second engagement element 32. The one or more engagement elements, such as the first engagement element 30 and/or the second engagement element 32, are configured for engagement with a coupling element 58 of the component 12 when the component 12 is positioned in the seat formed by the probe wall 22. The one or more engagement elements 30, 32, such as the first engagement element 30 and/or the second engagement element 32 is movable perpendicular to the main axis 100, such as in a radial direction. The one or more engagement elements 30, 32, such as the first engagement element 30 and/or the second engagement element 32 may also be movable in a direction parallel to the main axis 100, such as in a longitudinal direction.

The coupling member 38 in one of the first position and the second position, such as the second position, is configured to prevent the first engagement element 30 and/or the second engagement element 32 from moving to a release position such that the component 12 is locked to the probe 2. The coupling member 38 in the other of the first position and the second position, such as the first position, is configured to allow the first engagement element 30 and/or the second engagement element 32 to move to a release position such that the component 12 is not locked to the probe.

The probe wall 22 comprises a first cavity 40 at least partly accommodating the first engagement element 30. The probe wall 22 may comprises one or more cavities including the first cavity 40. The one or more cavities may at least partly accommodate the one or more engagement elements 30, 32. The one or more cavities may comprise a second cavity 44 at least partly accommodating the second engagement element 32.

The one or more engagement elements 30, 32 may be freely movable within the first cavity 40 and/or second cavity 44. This is particularly the case in the specifically depicted example, wherein the engagement elements 30, 32 are balls.

The first cavity 40 of FIG. 9 forms a first engagement stop 42 for the first engagement element, e.g. in a first engagement direction along a first engagement axis perpendicular to the main axis 100. The first engagement stop 42 may retain the first engagement element 30 in the first cavity 40. For example, when the first engagement element 30 is moved in the first engagement direction, the first engagement stop 42 may retain the first engagement element 30 in the first cavity 40. Thereby preventing the first engagement element 30 from being lost even if the component 12 is not positioned in the seat formed by the probe wall 22.

The second cavity 44 of FIG. 9 forms a first engagement stop 46 for the second engagement element, e.g. in a second engagement direction along a second engagement axis perpendicular to the main axis 100. The first engagement stop 46 may retain the second engagement element 32 in the second cavity 44. For example, when the second engagement element 32 is moved in the first engagement direction, the second engagement stop 46 may retain the second engagement element 32 in the second cavity 44, thereby preventing the second engagement element 32 from being lost, even if the component 12 is not positioned in the seat formed by the probe wall 22.

This feature may be especially relevant when the one or more engagement elements 30, 32 are balls, such as freely movable balls within the cavities 40, 44, as in the probe 2' depicted in FIG. 9.

The one or more engagement elements 30, 32 may be freely movable within the first cavity 40 and/or second cavity 44 when the coupling member 38 is in the first position. The one or more engagement elements 30, 32 may be restricted from moving within the first cavity 40 and/or second cavity 44 when the coupling member 38 is in the second position.

The coupling member 38 in the second position is configured to prevent the one or more engagement elements 30, 32, such as the first engagement element 30 and/or the second engagement element 32, from moving to a release position, e.g. when the component 12 is positioned in the seat formed by the probe wall 22.

The coupling member 38 in the first position is configured to allow the one or more engagement elements 30, 32, such as the first engagement element 30 and/or the second engagement element 32, to move to the release position.

The coupling member 38 and the probe body 4 may be configured to be attached to each other, such that the coupling member 38 is movable between positions, such as between the first position and the second position, but is retained attached to the probe body 4. For example, the coupling member 38 and/or the probe body 4 may comprise attachment members.

The coupling member 38 optionally comprises a primary attachment member 39, e.g. in the form of a protrusion as illustrated, and/or a plurality of attachment members including the primary attachment member 39. The probe body 4 optionally comprises a secondary attachment member 41, e.g. in the form of a recess as illustrated, and/or a plurality of secondary attachment members including the secondary attachment member. A primary attachment member, such as the primary attachment member 39, is configured to engage with a secondary attachment member, such as the secondary attachment member 41.

Provision of attachment members, such as primary attachment members and/or secondary attachment members, may provide that the coupling member may be click-locked to the probe body 4.

The component 12 comprises a coupling part 56 extending along the center axis 106. The coupling part has one or more coupling elements, such as a first coupling element 58 and a second coupling element 59 in an outer surface 60 for engagement with the one or more engagement elements 30, 32 of the locking mechanism 10. The coupling part 56 may have a plurality of coupling elements 58, 59 for engagement with a plurality of engagement elements 30, 32 of the locking mechanism 10. In the depicted example, the coupling elements 58, 59 are recesses configured for receiving the engagement elements 30, 32 being balls.

The locking mechanism 10 further comprises the coupling member 38 with the center axis 106. The coupling member 38 has a first position and a second position. The coupling member 38 may be configured to move from the first position to the second position and/or from the second position to the first position by rotation of the coupling member 38 in relation to the probe body 4 about the center axis 106. For example, the coupling member 38 may be rotated from the first position to the second position and/or from the second position to the first position with an angular displacement in the range of 10° to 360°, such as in the range of 10° to 40°, such as in the range of 20° to 30°, such as 25°.

Alternatively or additionally, the coupling member 38 may be configured to move from the first position to the second position and/or from the second position to the first position by movement of the coupling member along the main axis 100 in relation to the probe body 4. Movement of the coupling member 38 along the main axis 100 may be caused by simultaneous rotation of the coupling member 38 in relation to the probe body 4 about the center axis 106. Alternatively, movement of the coupling member 38 along the main axis 100 may be independent of rotation of the coupling member 38.

Figure 10:
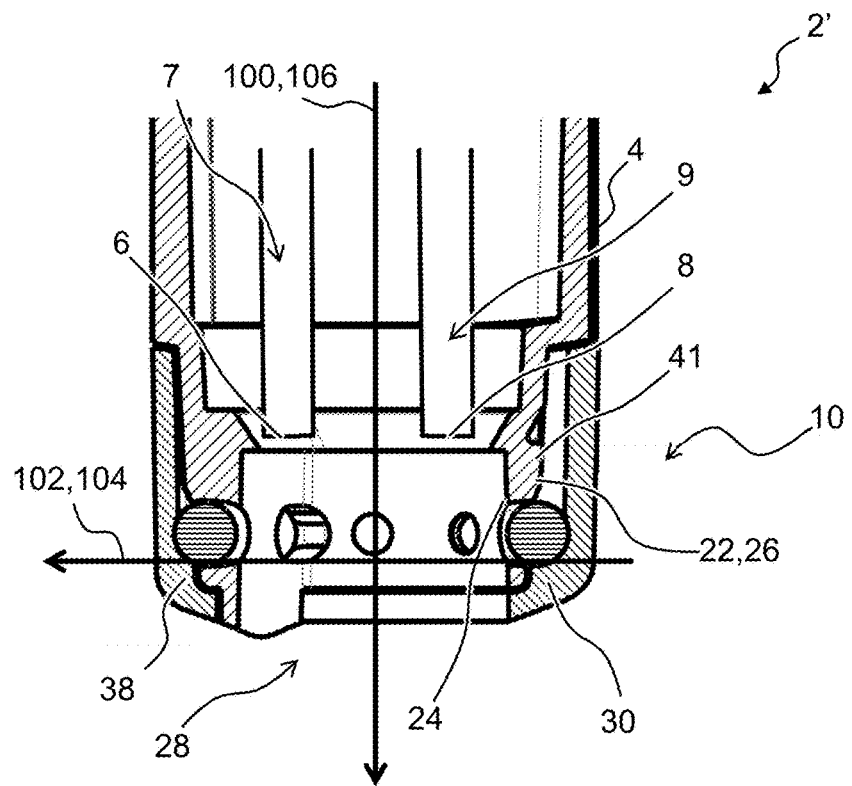
FIG. 10 is a longitudinal section of an exemplary probe.

FIG. 10 is a longitudinal section of an exemplary probe 2'. The probe 2' comprises a probe body 4 with a first probe opening 6 to a first probe channel 7 in the probe body 4. In the depicted example, the probe 2' further comprises a second probe opening 8 to a second probe channel 9.

The probe 2' comprises a locking mechanism 10 for connecting a component (FIG. 1 and FIG. 9). The locking mechanism 10 comprises a probe wall 22 extending along a main axis 100 and having an inner surface 24 and an outer surface 26. The probe wall 22 forms a seat 28 for receiving the component. The probe wall 22 surrounds the first probe opening 6. The probe body 4 comprises a second probe opening 8 to a second probe channel 9. The probe wall 22 surrounds the second probe opening 8.

The locking mechanism 10 further comprises one or more engagement elements including a first engagement element 30 for engagement with a coupling element of the component. The first engagement element 30 is movable along a first engagement axis 102, e.g. in a first engagement direction 104. The first engagement axis 102 is perpendicular to the main axis 100. The first engagement axis 102 may alternatively be substantially perpendicular to the main axis, such as between 80° and 100°.

The locking mechanism 10 further comprises a coupling member 38 with a center axis 106. The locking mechanism 10 is configured to lock the component to the probe body 4 depending on the position of the coupling member 38, e.g. the locking mechanism 10 may be configured to lock the component to the probe body 4 when the coupling member 38 is in one position, and the locking mechanism 10 may be configured to not lock the component to the probe body 4 when the coupling member 38 is in another position.

The coupling member 38 has a first position and a second position. The coupling member 38 in the first position is configured to allow the first engagement element 30 to move to a release position. The coupling member 38 in the second position is configured to prevent the first engagement element 30 from moving to the release position.

The first engagement element 30 may be movable in a first release direction along the engagement axis 102. The first release direction may be opposite the first engagement direction 104.

Figures 11A, 11B:
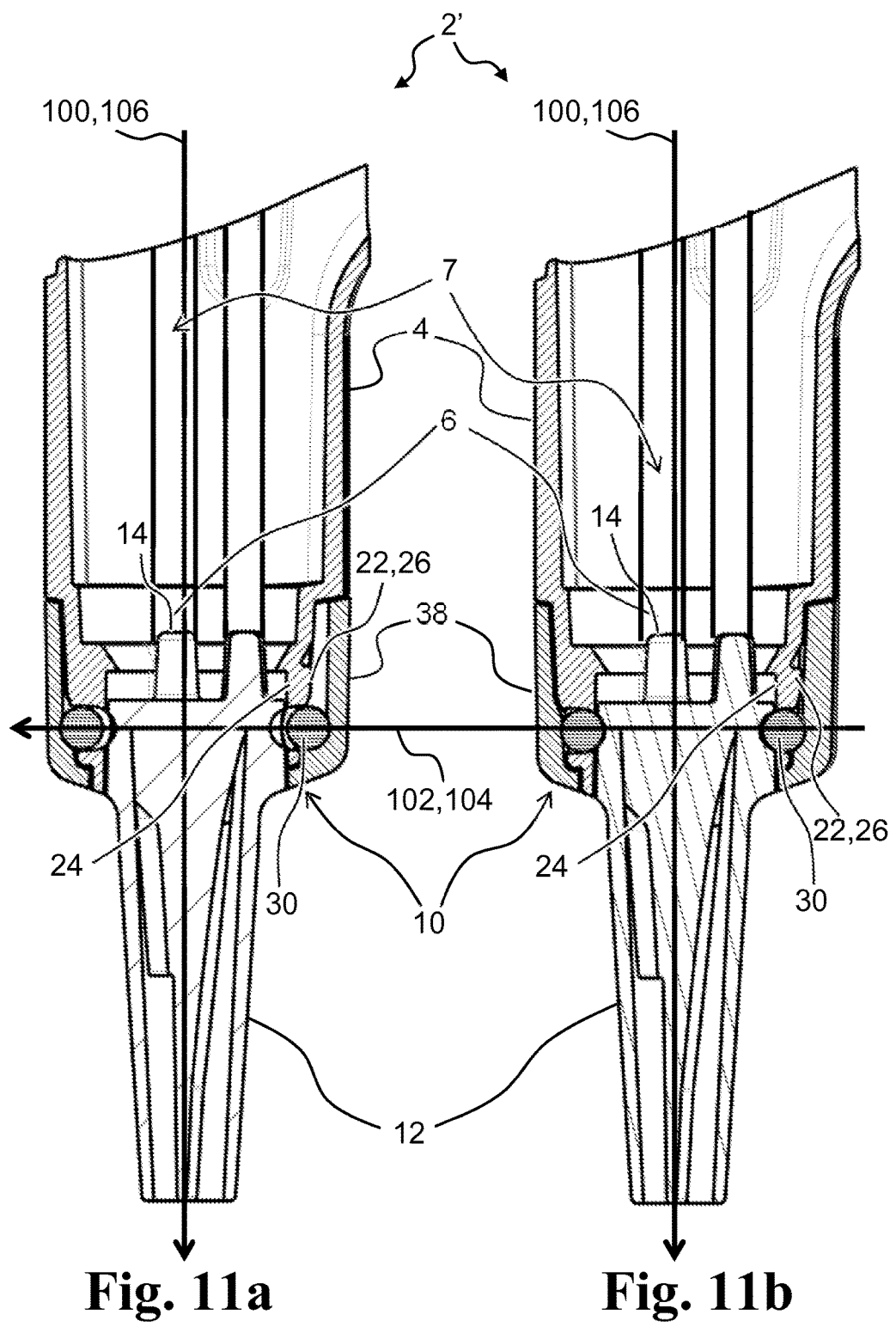
FIG. 11a-b is longitudinal sections of an exemplary probe with a component.

FIG. 11a and FIG. 11b are longitudinal sections of an exemplary probe 2' with an attached component 12.

In FIG. 11a, the first engagement element 30 is in a release position, wherein the component 12 is movable relative to the probe body 4 along the main axis 100. The component 12 may be detached from the probe body 4 when the first engagement element 30 is in the release position, as illustrated in FIG. 11a. In FIG. 11b, the first engagement element 30 is in an engagement position, wherein the component 12 is restricted from moving relative to the probe body 4 along the main axis 100. The component 12 is locked to the probe body 4 when the first engagement element 30 is in the engagement position, as illustrated in FIG. 11b.

The first engagement element 30 in the release position, as shown in FIG. 11a, is movable in a first engagement direction 104 along a first engagement axis 102. The first engagement axis 102 is perpendicular to the main axis 100. The first engagement element 30 in the release position may be moved to the engagement position, as shown in FIG. 11b, in the first engagement direction 104 along the first engagement axis 102.

In FIG. 11a, the coupling member 38 is in the first position, and in FIG. 11b the coupling member 38 is in the second position. The coupling member 38 in the first position (FIG. 11a) allows the first engagement element 30 to move along a first engagement axis 102, e.g. the coupling member 38 in the first position (FIG. 11a) allows the first engagement element 30 to move between the release position and the engagement position. The coupling member 38 in the second position (FIG. 11b) prevents the first engagement element 30 to move along the first engagement axis 102, e.g. the coupling member 38 in the second position (FIG. 11b) locks the first engagement element 30 in the engagement position.

The first engagement axis 102 is perpendicular to the main axis 100, and/or spanning an angle between 80° and 100°. The first engagement element 30 may move from the release position to the engagement position in a first engagement direction 104 along the first engagement axis 102. The first engagement element 30 may move from the engagement position to the release position in a first release direction, e.g. opposite the first engagement direction 104, along the first engagement axis 102.

The first engagement element 30 shown in the depicted example is a ball freely movable within the cavity formed by the probe wall 22 and the coupling member 38. When the coupling member 38 is in the first position (FIG. 11a), the first engagement element 30 is freely movable along the engagement axis 102, e.g. between an engagement position and a release position. When the coupling member 38 is in the second position (FIG. 11b), the first engagement element 30 is in the engagement position and restricted in moving along the engagement axis 102 to the release position. When the coupling member 38 is in the first position (FIG. 11a) the first engagement element 30 is movable along the engagement axis 102 to the release position. Movement of the engagement element 30 to the release position may be caused by a user removing the component 12 from the probe body 4.

In FIGS. 11a and 11b it is further illustrated that the component 12 comprises a first component opening 14 to a first component channel 16.

Figure 12:
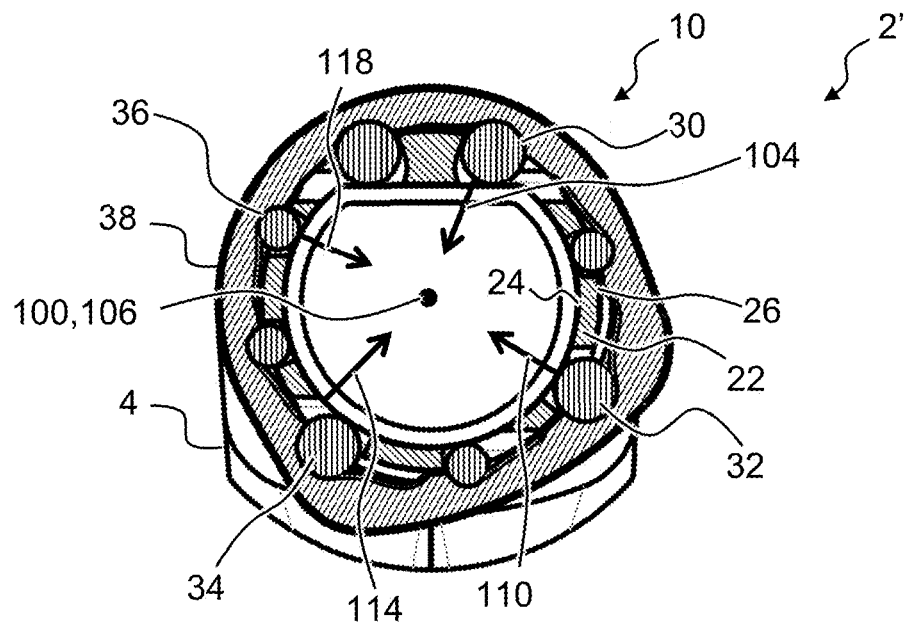
FIG. 12 is a cross section of an exemplary probe with a coupling member in a first position.

FIG. 12 is a cross section of an exemplary probe 2' with a coupling member 38 in a first position. The locking mechanism 10 of the exemplary probe 2' comprises one or more engagement elements 30, 32, 34, 36. In the depicted example, the locking mechanism 10 comprises a first engagement element 30, a second engagement element 32, a third engagement element 34, and a fourth engagement element 36.

The one or more engagement elements 30, 32, 34, 36 has an engagement position and a release position. In FIG. 12, the one or more engagement elements 30, 32, 34, 36 are in their release positions. In their release positions, the one or more engagement elements 30, 32, 34, 36 do not protrude from the inner surface 24 of the probe wall 22.

The coupling member 38 in the first position, as shown in FIG. 12, allows the one or more engagement elements 30, 32, 34, 36 to move between their engagement positions and their release positions. In the depicted example, the one or more engagement elements 30, 32, 34, 36 are shown in their release position. The one or more engagement elements 30, 32, 34, 36 may move to the release position due to bias, e.g. the engagement elements 30, 32, 34, 36 are biased towards their release position, or the one or more engagement elements 30, 32, 34, 36 may be pushed to their release position by the component being removed from the probe body 4, e.g. by coupling elements of the component having a tapered surface.

The first engagement element 30 is movable in a first engagement direction 104 along a first engagement axis perpendicular to the main axis 100. The first engagement element 30 is movable in the first engagement direction 104 from the release position to the engagement position.

The second engagement element 32 is movable in a second engagement direction 110 along a second engagement axis perpendicular to the main axis 100. The second engagement element 32 is movable in the first engagement direction 110 from the release position to the engagement position.

The third engagement element 34 is movable in a third engagement direction 114 along a third engagement axis perpendicular to the main axis 100. The third engagement element 34 is movable in the third engagement direction 114 from the release position to the engagement position.

The fourth engagement element 36 is movable in a fourth engagement direction 118 along a fourth engagement axis perpendicular to the main axis 100. The fourth engagement element 36 is movable in the fourth engagement direction 118 from the release position to the engagement position.

One or more of the first, second, third, and/or fourth engagement elements 30,32,34,36 may also be movable in one or more directions not perpendicular to the main axis 100.

Furthermore, FIG. 12 shows that the inner surface 24 of the probe wall 22 has a non-circular cross section. Specifically in the depicted example, the probe wall 22 comprises a circular part, or part of a circle, and a straight part. Thereby, the shape of the probe wall prevents rotation and misalignment of the component when the component is inserted in the seat formed by the probe wall.

As also illustrated, the one or more engagement elements 30, 32, 34, 36 may be different sized balls. For example, as shown in this example, the diameter of the first engagement element 30 is larger than the diameter of the fourth engagement element 36.

Figure 13:
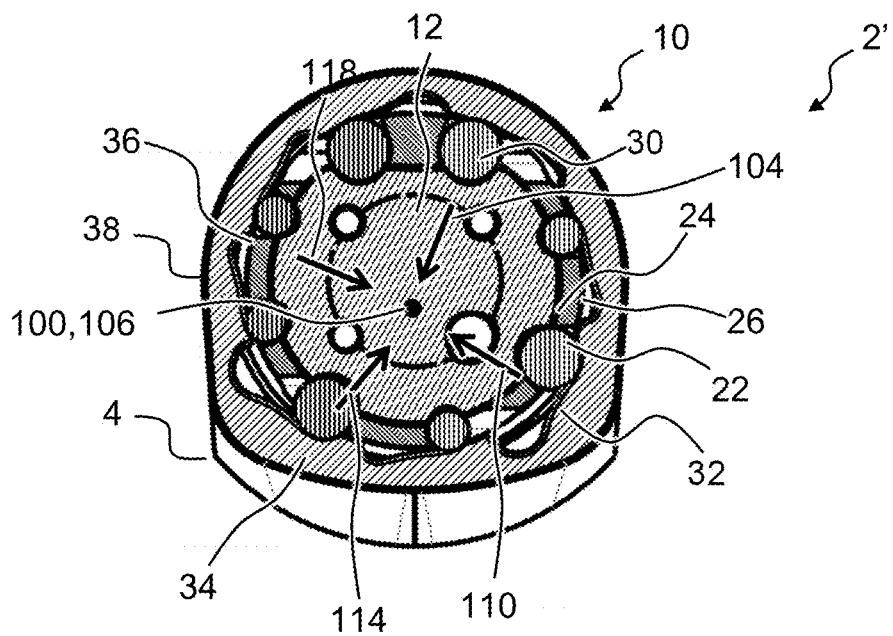
FIG. 13 is a cross section of an exemplary probe with a coupling member in a second position.

FIG. 13 is a cross section of the exemplary probe 2' of FIG. 12 with the coupling member 38 in a second position. In FIG. 13 a component 12 has been positioned in the seat formed by the probe wall 22.

The coupling member 38 has been moved from the first position, as illustrated in FIG. 12, to the second position, as illustrated in FIG. 13, by rotation of the coupling member 38 in relation to the probe body 4 about the center axis 106 of the coupling member 38. The coupling member 38 is rotated from the first position to the second position with an angular displacement of approximately 25°.

In FIG. 13, the one or more engagement elements 30, 32, 34, 36 are in their respective engagement positions. In their engagement positions, the one or more engagement elements 30, 32, 34, 36 may form a protrusion from the inner surface 24 of the probe wall 22 in their respective engagement directions 104, 110, 114, 118, e.g. perpendicular to the main axis 100. In their engagement positions, the one or more engagement elements 30, 32, 34, 36 engage with coupling elements of the component 12.

In the depicted example, upon moving the coupling member 38 from the first position (FIG. 12) to the second position (FIG. 6), the coupling member 38 is configured to cause the one or more engagement elements, such as the first engagement element 30, the second engagement element 32, the third engagement element 34, and/or the fourth engagement element 36, to move to their engagement positions, e.g. in their respective engagement directions 104, 110, 114, 118.

Figure 14:
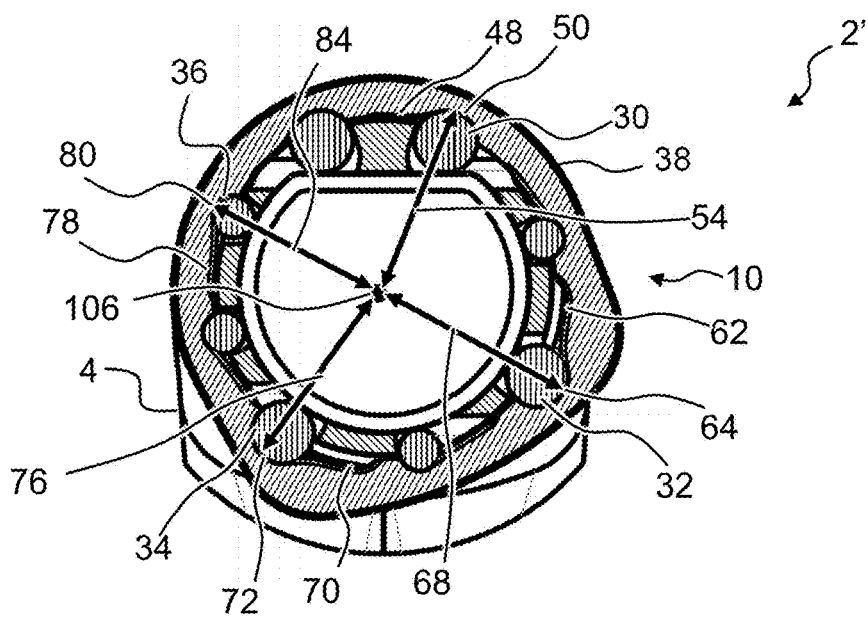
FIG. 14 is a cross section of an exemplary probe with a coupling member in a first position.
Figure 15:
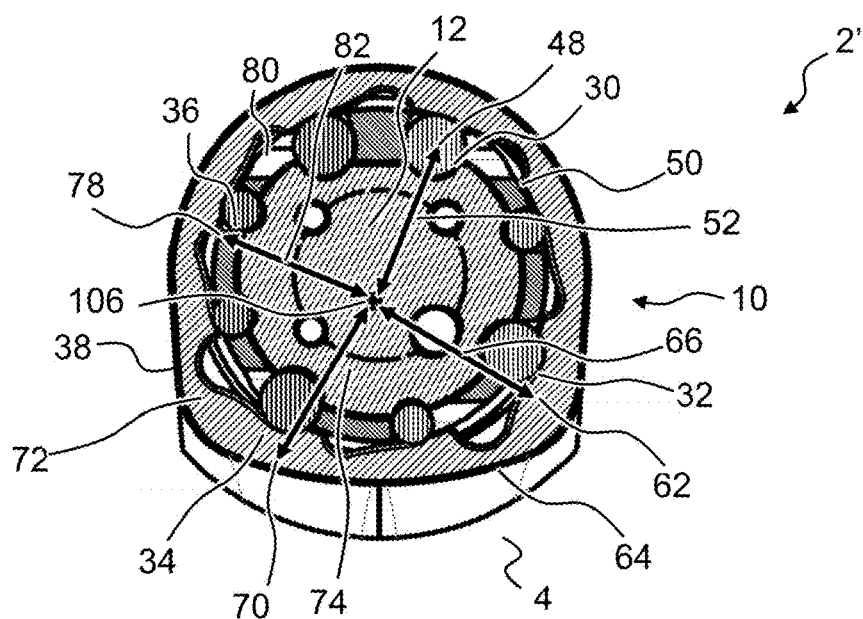
FIG. 15 is a cross section of an exemplary probe with a coupling member in a second position.

FIGS. 14 and 15 are cross sections of the exemplary probe 2' of FIGS. 12-13 with the coupling member 38 in the first position (FIG. 14) and second position (FIG. 15). In FIG. 15 a component 12 has been positioned in the seat formed by the probe wall 22.

The coupling member 38 comprises one or more lock stops 48, 62, 70, 78 for the one or more engagement elements 30, 32, 34, 36. The coupling member 38 comprises a first lock stop 48 for the first engagement element 30. The coupling member 38 comprises a second lock stop 62 for the second engagement element 32. The coupling member 38 comprises a third lock stop 70 for the third engagement element 34. The coupling member 38 comprises a fourth lock stop 78 for the fourth engagement element 36.

The coupling member 38 comprises one or more release stops 50, 64, 72, 80 for the one or more engagement elements 30, 32, 34, 36. The coupling member 38 comprises a first release stop 50 for the first engagement element 30. The coupling member 38 comprises a second release stop 64 for the second engagement element 32. The coupling member 38 comprises a third release stop 72 for the third engagement element 34. The coupling member 38 comprises a fourth release stop 80 for the fourth engagement element 36.

The one or more release stops 50, 64, 72, 80 are configured to form stops for the one or more engagement elements 30, 32, 34, 36 in a direction opposite their respective engagement directions when the coupling member 38 is in the first position, as shown in FIG. 14.

The one or more lock stops 48, 62, 70, 78 are configured to form stops for the one or more engagement elements 30, 32, 34, 36 in a direction opposite their respective engagement directions when the coupling member 38 is in the second position, as shown in FIG. 15.

The one or more lock stops 48, 62, 70, 78 have respective lock distances 52, 66, 74, 82 to the center axis. The one or more release stops 50, 64, 72, 80 have respective release distances 54, 68, 76, 84 to the center axis. A release distance 54, 68, 76, 84 is larger than its respective lock distance 52, 66, 74, 82.

The first lock stop 48 has a first lock distance 52 to the center axis 100. The first release stop 50 has a first release distance 54 to the center axis. The first release distance 54 is larger than the first lock distance 52.

The second lock stop 62 has a second lock distance 66 to the center axis 100. The second release stop 64 has a second release distance 68 to the center axis. The second release distance 68 is larger than the second lock distance 66.

The third lock stop 70 has a third lock distance 74 to the center axis 100. The third release stop 72 has a third release distance 76 to the center axis. The third release distance 76 is larger than the third lock distance 74.

The fourth lock stop 78 has a fourth lock distance 82 to the center axis 100. The fourth release stop 80 has a fourth release distance 84 to the center axis. The fourth release distance 84 is larger than the fourth lock distance 82.

The coupling member 38 may comprise a gradual transition, as shown in FIGS. 14 and 15, between a lock stop 48, 62, 70, 78 and its respective release stop 50, 64, 72, 80, such that upon moving the coupling member 38 from the first position to the second position, the coupling member 38 causes the one or more engagement elements, such as the first engagement element 30, the second engagement element 32, the third engagement element 34, and/or the fourth engagement element 36, to move from their release positions to their engagement positions, e.g. to move in their respective engagement directions.

As illustrated in the above figures and examples, the main axis 100 and the center axis 106 may be the same axis. However, the main axis 100 and the center axis 106 may conversely be different axes, e.g. the main axis 100 and the center axis 106 may span an angle with a magnitude more than 0°.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 2, 2' probe
4 probe body
6 first probe opening
7 first probe channel
8 second probe opening
9 second probe channel
10, 10' locking mechanism
12 component
14 first component opening
16 first component channel
18 second component opening
20 second component channel
22 probe wall
24 inner surface of probe wall
26 outer surface of probe wall
28 seat
30 first engagement element
32 second engagement element
34 third engagement element
36 fourth engagement element
38 coupling member
39 primary attachment member
40 first cavity
41 secondary attachment member
42 first engagement stop for first engagement element
44 second cavity
46 first engagement stop for second engagement element
48 first lock stop
50 first release stop
52 first lock distance
54 first release distance
56 coupling part
58 first coupling element
59 second coupling element
60 outer surface of coupling part
62 second lock stop
64 second release stop
66 second lock distance
68 second release distance
70 third lock stop
72 third release stop
74 third lock distance
76 third release distance
78 fourth lock stop
80 fourth release stop
82 fourth lock distance
84 fourth release distance
100 main axis
102 first engagement axis
104 first engagement direction
106 center axis
108 second engagement axis
110 second engagement direction
112 third engagement axis
114 third engagement direction
116 fourth engagement axis
118 fourth engagement direction

The invention claimed is:

1. A probe for conducting an audiologic test, the probe comprising:
a probe body with a plurality of probe openings associated with a plurality of probe channels in the probe body, the probe body includes a probe wall extending along a main axis, the probe wall having an inner surface and an outer surface and one or more engagement elements positioned on the inner surface of the probe wall wherein a first engagement element is movable along a first engagement axis perpendicular to the main axis;
a component having a first component opening associated with a first component channel, the component having a coupling part extending along a center axis and one or more coupling elements for engagement with the one or more engagement elements of the probe body, the coupling part of the component positioned on the inner surface of the probe wall; and
a coupling member with the center axis positioned between the probe body and the component the coupling member having a primary attachment member, one or more lock stops and one or more release stops, the coupling member being moveable to a first position and to a second position by rotation of the coupling member in relation to the probe body, wherein the coupling member, the probe wall with the one or more engagement elements and the one or more coupling elements form a locking mechanism to lock the component to the probe body when the coupling member moves from the first position to the second position and the one or more engagement elements engages with the one or more coupling elements of the component.

2. The probe according to claim 1, wherein the coupling member in the second position prevents the first engagement element from moving to a release position along the first engagement axis and locks the component to the probe body.

3. The probe according to claim 1, wherein the probe wall having a plurality of cavities at least partly accommodating first engagement element, each of the plurality of cavities forming a first engagement stop for the first engagement element.

4. The probe according to claim 1, wherein the one or more engagement elements comprise a second engagement element for engagement with an additional coupling element of the component, wherein the second engagement element is movable along a second engagement axis perpendicular to the main axis when the coupling member is in the first position; and wherein the coupling member in the second position prevents the second engagement element from moving to a release position along the second engagement axis.

5. The probe according to claim 1, wherein the coupling member comprises a first lock stop for the first engagement element when the coupling member is in the second position.

6. The probe according to claim 5, wherein the coupling member comprises a first release stop for the first engagement element when the coupling member is in the first position, wherein the first release stop is at a first release distance from the center axis, and the first lock stop is at a first lock distance from the center axis, wherein the first release distance is larger than the first lock distance.

7. The probe according to claim 1, wherein the probe wall has a non-circular cross section.

8. The probe according to claim 1, wherein the one or more engagement elements comprise a second engagement element, a third engagement element, and a fourth engagement element.

9. The probe according to claim 1, wherein the probe body has each of the plurality of probe openings associated with each of the plurality of probe channels in the probe body, and wherein the probe wall surrounds each of the plurality of probe openings.

10. The probe according to claim 1, wherein the coupling member is configured to prevent the first engagement element from moving radially outward from a longitudinal axis of the probe when the coupling member is in the second position.

* * * * *